US00PP20938P2

(12) United States Plant Patent
Hoogenraad

(10) Patent No.: US PP20,938 P2
(45) Date of Patent: Apr. 20, 2010

(54) ***CEANOTHUS* PLANT NAMED 'LEMON ICE'**

(50) Latin Name: ***Ceanothus* hybrid**
Varietal Denomination: Lemon Ice

(76) Inventor: Gerrit Hoogenraad, Rijksweg 30A, 6744 WB Ederveen (NL)

( * ) Notice: Subject to any disclaimer, the term of this patent is extended or adjusted under 35 U.S.C. 154(b) by 0 days.

(21) Appl. No.: 12/321,683

(22) Filed: Jan. 23, 2009

(51) Int. Cl.
*A01H 5/00* (2006.01)

(52) U.S. Cl. ..... Plt./226

(58) Field of Classification Search ..... Plt./226

See application file for complete search history.

*Primary Examiner*—Susan B McCormick Ewoldt
(74) *Attorney, Agent, or Firm*—Penny J. Aguirre

(57) ABSTRACT

A new cultivar of *Ceanothus*, 'Lemon Ice', characterized by its variegated foliage with dark green centers and wide yellow margins and its panicles of sweetly fragrant light blue flowers.

2 Drawing Sheets

Botanical classification: *Ceanothus* hybrid.
Variety denomination: 'Lemon Ice'.

BACKGROUND OF THE INVENTION

The present invention relates to a new and distinct cultivar of *Ceanothus* of hybrid origin, and will be referred to hereafter by its cultivar name, 'Lemon Ice'. 'Lemon Ice' is a new cultivar of deciduous shrub for use as a landscape plant.

The new cultivar of *Ceanothus* was discovered as a naturally occurring branch mutation of *Ceanothus* 'Blue Mound' (not patented) in a container in the Inventor's nursery in June of 2004 in Ederveen, The Netherlands. *Ceanothus* 'Blue Mound' is believed to be a hybrid of C. *thyrsiflorus* var. *griseus* and C. *impressus*.

Asexual reproduction of the new cultivar was first accomplished using terminal stem cuttings by the Inventor in Ederveen, The Netherlands in August 2004. The characteristics of this cultivar have been determined to be stable and are reproduced true to type in successive generations.

SUMMARY OF THE INVENTION

The following traits have been repeatedly observed and represent the characteristics of the new cultivar as grown outdoors in 10 liter containers for four years in Ederveen, The Netherlands. These attributes in combination distinguish 'Lemon Ice' as a new and unique cultivar of *Ceanothus*.

1. 'Lemon Ice' produces variegated leaves with dark green centers and wide yellow margins.
2. 'Lemon Ice' produced panicles of sweetly fragrant light blue flowers.

The closest comparison plant to 'Lemon Ice' is the parent plant, 'Blue Mound'. 'Blue Mound' differs from 'Lemon Ice' in having leaves that are non variegated. 'Lemon Ice' can also be compared to the cultivar 'Perado' (U.S. Plant Pat. No. 13,433). 'Perado' is similar to 'Lemon Ice' in having variegated foliage, however 'Perado' differs by having leaves that are smaller in size and flowers that are blue-violet in color while the flowers of 'Lemon Ice' are lighter blue and less violet in color.

BRIEF DESCRIPTION OF THE DRAWING

The accompanying colored photographs illustrates the overall appearance and distinct characteristics of a 4 year-old plant of the new *Ceanothus* as grown outdoors in a 10-liter container in Ederveen, The Netherlands.

The photograph

Figure 1:
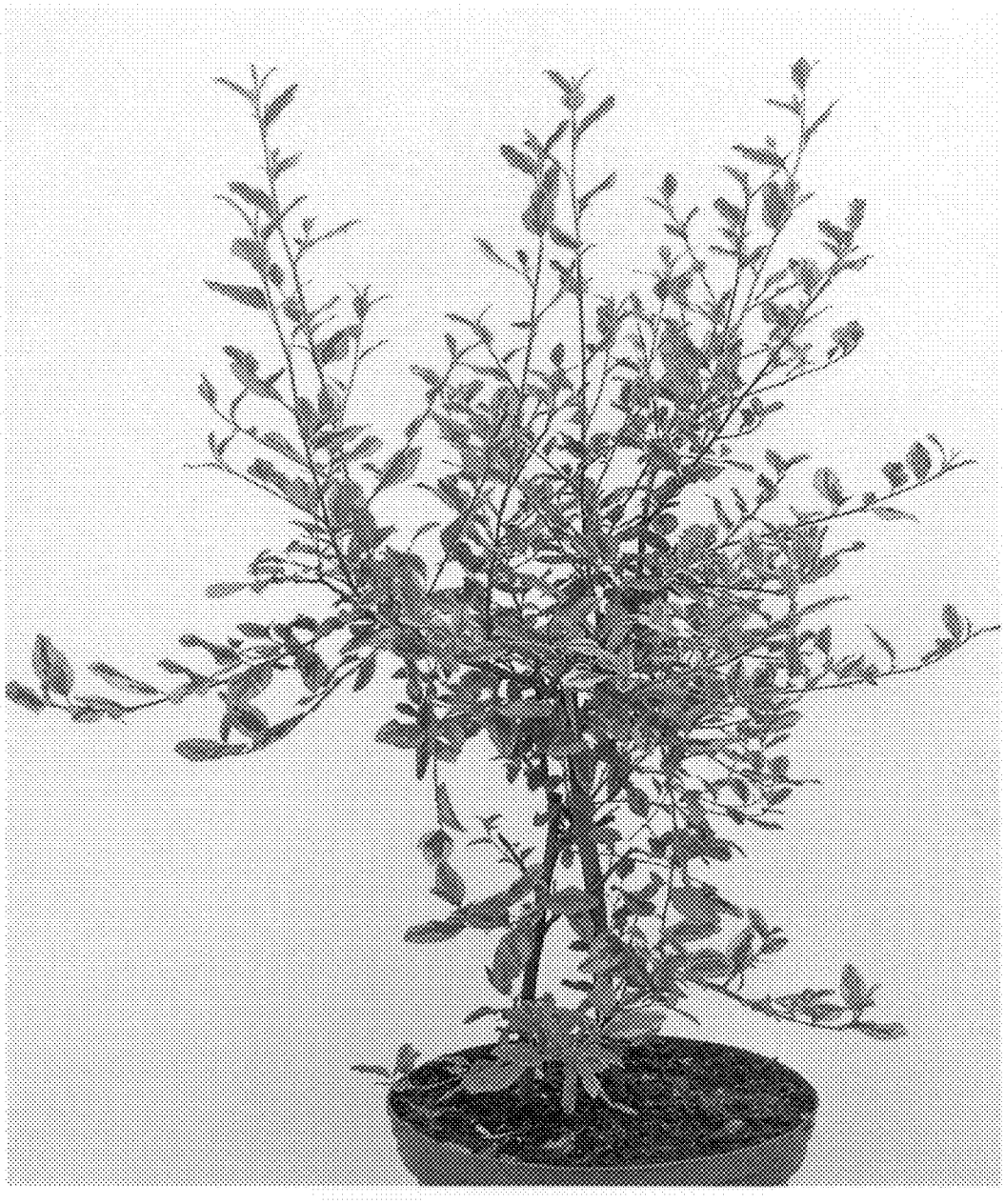
FIG. 1 is a side view and illustrates the overall habit and foliage coloration of 'Lemon Ice'.
Figure 2:
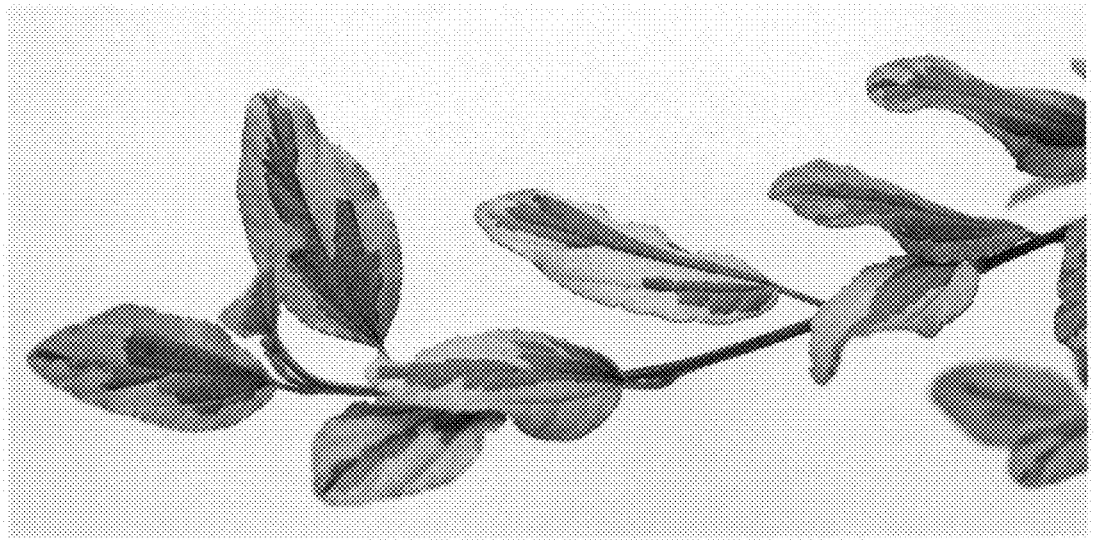
Figure 3:
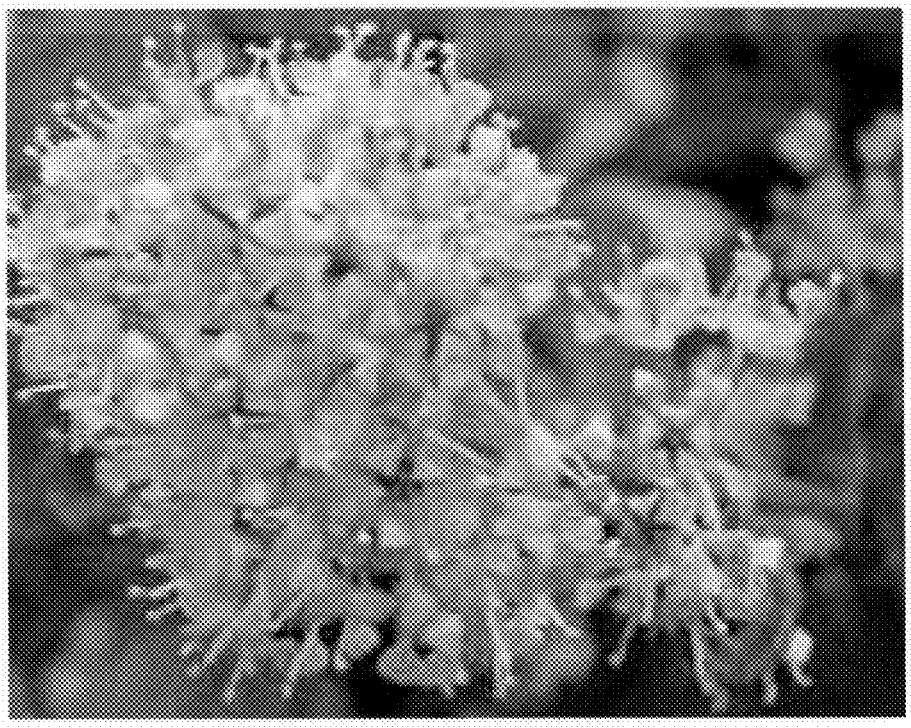

The photograph in FIG. 2 provides a close-up view of the foliage and variegation pattern of 'Lemon Ice' and the photograph in FIG. 3 provides a close-up view of the flowers of 'Lemon Ice'.

The colors in the photograph may differ slightly from the color values cited in the detailed botanical description, which accurately describe the colors of the new *Ceanothus*.

DETAILED BOTANICAL DESCRIPTION

The following is a detailed description of 4 year-old plants of the new *Ceanothus* as grown outdoors in 10-liter containers in Ederveen, The Netherlands. The phenotype of the new cultivar may vary with variations in environmental, climatic, and cultural conditions, as it has not been tested under all possible environmental conditions. The color determination is in accordance with the 2007 R.H.S. Colour Chart of The Royal Horticultural Society, London, England, except where general color terms of ordinary dictionary significance are used.

General plant characteristics:

*Plant type.*—Deciduous, perennial shrub.

*Plant habit.*—Upright, spreading.

*Blooming period.*—Spring (May), occasional repeat flowering occurs in September and October.

*Height and spread.*—Average of 74 cm in height and 55 cm in width in a 10-liter container.

*Cold hardiness.*—At least to U.S.D.A. Zone 7b.

*Diseases and pests.*—No susceptibility or resistance to diseases or pests has been observed.

*Root description.*—Fibrous.

Growth and propagation:

*Propagation.*—Terminal stem cuttings, roots appear in about 45 days at 20° .

*Growth rate.*—Moderate to vigorous, an annual growth rate of about 25 cm per year.

Stem description:

*Shape.*—Rounded, with 5 indistinct angles.

*Stem color.*—New twigs; 143A to 143B, mature bark; color between N200A and N200B.

*Stem strength.*—Very strong.

*Stem surface.*—Glabrous, slightly glossy.

*Stem size.*—Lateral branches average 22.8 cm in length and an average of 2 mm in diameter, pinching is not required but will improve the number of branches.

*Branching.*—Freely branched; average of 35 lateral branches.

*Branch internode length.*—About 2.4 cm.

Foliage description:

*Leaf shape.*—Ovate to elliptic.

*Leaf division.*—Simple.

*Leaf base.*—Cuneate.

*Leaf apex.*—Rounded.

*Leaf fragrance.*—None.

*Leaf venation.*—Pinnate, the vein color reflects the color of the leaf; upper surface N137A to 139A in color on the leaf center and N144D in color on the leaf margin, lower surface 144A to 144B.

*Leaf margins.*—Entire, undulate, finely serrate with about 6 serration per cm.

*Leaf arrangement.*—Alternate.

*Leaf attachment.*—Petiolate.

*Leaf number.*—Average of 10 per lateral branch.

*Leaf surface.*—Smooth, very slightly glossy.

*Leaf size.*—Average of 3.5 cm in length and 1.8 cm in width.

*Leaf internode length.*—Average of 2 cm.

*Leaf variegation pattern.*—Margins are wide but irregular in pattern.

*Leaf color.*—Newly expanded leaves upper surface; centers 139A with margins 144B to 145A, newly expanded leaves lower surface; centers 137B with margins 143C, mature leaves upper surface; centers N137A to 139A with margins N144D, mature leaves lower surface; centers 137B with margins 143C.

*Petioles.*—Average of 9 mm in length and 1.5 mm in width, 145A in color, surface is smooth and glabrous.

*Stipules.*—None observed.

Inflorescence description:

*Inflorescence type.*—Compound axillary and terminal panicles consisting of simple umbels.

*Inflorescence number.*—About 10 on a 4 year-old plant.

*Inflorescence size.*—Averages 2.8 cm in height and 1.9 cm in width.

*Flower quantity.*—About 48 per inflorescence.

*Flowering season.*—Spring (May in The Netherlands), occasional repeat in autumn (September and October).

*Response time to flower.*—Approximately 8 months.

*Pedicels.*—About 7 mm length and 0.5 mm in diameter, 143B to 143C in color, tinged 100C near the calyx, moderately strong, held at a 45° to 90° angle to peduncle.

*Peduncle.*—About 4.8 cm in length and 1 mm in diameter, held upright to stem.

*Flower buds.*—Globular in shape, 2 mm in depth and 4 mm in diameter 101C to 101D in color, buds open in approximately 4 days from described stage.

*Flower fragrance.*—Slightly fragrant, sweet.

*Persistence of flowers.*—Self-cleaning.

*Lastingness of flowers.*—Flowers last about 1 week.

*Flower type.*—Single, star shaped with spreading petals.

*Flower aspect.*—Outward to upright.

*Flower shape.*—Rotate.

*Flower size.*—About 4 mm in diameter and 3 mm in depth.

*Petals.*—5, about 2.5 mm in length and 1.25 in width, petals not fused, oblanceolate in and concave in shape, margin entire, apex obtuse, rotate arrangement, surface smooth, color of newly opened upper and lower surfaces; 101C, base 101D, fully opened upper and lower surfaces; 101C to 101D with base lighter than 101D, mature petals fade to a color lighter than 101D.

*Sepals.*—5, about 2.5 mm in length and 1.5 mm in width, rotate arrangement with lower 20% fused, surface is dull and glabrous, ovate in shape, margin entire, tip broadly acute, color of immature upper and lower surface 94C, color of mature upper and lower surface 94D.

*Calyx.*—Rotate in shape, about 2.5 mm in length and 3 mm in diameter.

*Fruits and seeds.*—Seed production has not been seen to date.

Reproductive organs:

*Gynoecium.*—Pistils1, about 1 mm in length, stigma cleft (3 parted) and 94D in color, style is about 0.5 mm in length and 94D in color, ovary is 147 to 147 B in color.

*Androcoecium.*—Average of 5, anthers are basifixed, broadly ovate and about 0.5 mm in length, filaments are about 3 mm in length and 4D in color, pollen moderately produced and 4C in color.

*Fruits and seeds.*—No fruit or seed set has been observed.

It is claimed:

1. A new and distinct cultivar of *Ceanothus* plant named 'Lemon Ice', as herein illustrated and described.

* * * * *